United States Patent [19]

Calvo

[11] 4,216,201
[45] Aug. 5, 1980

[54] COSMETIC EMULSION COMPOSITIONS HAVING SKIN MOISTURIZING PROPERTIES

[75] Inventor: Luis C. Calvo, Bayshore, N.Y.

[73] Assignee: Germaine Monteil Cosmetiques Corp., Deer Park, N.Y.

[21] Appl. No.: 908,178

[22] Filed: May 22, 1978

[51] Int. Cl.$^2$ .................................................. A61K 7/021
[52] U.S. Cl. ..................................... 424/63; 424/168; 424/365
[58] Field of Search .......................... 424/63, 365, 168

[56] References Cited

U.S. PATENT DOCUMENTS

| | | | |
|---|---|---|---|
| 3,088,874 | 5/1963 | Geary et al. | 424/68 X |
| 3,846,546 | 11/1974 | Lachampt et al. | 424/365 X |
| 3,846,556 | 11/1974 | Handjani et al. | 424/63 X |
| 3,926,840 | 12/1975 | Wendler et al. | 424/172 X |
| 4,035,513 | 7/1977 | Kumano | 424/172 X |
| 4,073,743 | 2/1978 | Midler, Jr. et al. | 424/172 X |

OTHER PUBLICATIONS

Spalton, Pharmaceutical Emulsions & Emulsifying Agents, 8/1950, pp. 4 to 10, 16 to 19,26,28,36, 52 to 54,56,98,117,119 & 123.

de Navarre, International Encyclopedia of Cosmetic Material Trade Names, 6/1957, pp. 257.

*Primary Examiner*—Dale R. Ore
*Attorney, Agent, or Firm*—Wolder, Gross & Yavner

[57] ABSTRACT

A cosmetic emulsion base for stable, appealing cosmetic creams and lotions having excellent skin moisturizing properties is provided in the form of a water in oil (W/O) emulsion wherein 60 to 80% by weight of water is dispersed and stabilized in an external oil phase comprising 15 to 25% straight chain hydrocarbons of desired oiliness and consistency and including branched chain hydrocarbon oil components to aid skin penetration, a mixture of emulsifier components comprising about 5 to 10% of the compositions and consisting essentially of 1 esters of fatty acids containing twelve to eighteen carbon atoms and polyhydric alcohols containing three to ten carbon atoms and lesser amounts of a di- or tri-valent metallic soap. As applied to the skin the W/O emulsions enhance moisture penetration of the skin while minimizing loss by evaporation, and may provide excellent carriers of cosmetic covering and coloring agents in amounts up to about 10% by weight of the composition.

6 Claims, No Drawings

COSMETIC EMULSION COMPOSITIONS HAVING SKIN MOISTURIZING PROPERTIES

This invention relates to a cosmetic base for stable, appealing cosmetic creams and lotions having excellent skin moisturizing properties in the form of a water in oil (W/O) emulsion wherein 60 to 80% by weight of water is dispersed and stabilized in an external oil phase comprising 15 to 25% straight chain hydrocarbons of desired oiliness and consistency and including branched chain hydrocarbon components to aid skin penetration, by a mixture of emulsifier components comprising about 5 to 10% of the composition and consisting essentially of esters of fatty acids containing twelve to eighteen carbon atoms and polyhydric alcohols containing three to ten carbon atoms and lesser amounts of a di- or tri-valent metallic soap. As applied to the skin the W/O emulsions enhance moisture penetration of the skin while minimizing loss by evaporation, and may provide excellent carriers of cosmetic covering and coloring agents in amounts up to about 10% by weight of the composition.

BACKGROUND OF THE INVENTION

Cosmetic make-up compositions intended to apply coatings and/or colors to the skin generally fall into one of the categories: A - Dry powders in loose, cake, or compact form, B - Anhydrous fatty systems (oils and waxes) in solid, paste and liquid forms, and C - Emulsions of the oil-in-water (O/W) type in cream and lotion forms. The compositions in categories A and B do not provide moisture to the skin at all. While compositions in category C are intended to apply moisture to the skin, there is considerable loss of moisture due to evaporation during application and feathering of the composition, or within a short period after application due to the moisture being in the outer phase of the emulsion.

This shortcoming of the O/W type emulsion should in theory be overcome by switching to a water-in-oil (W/O) type emulsion, but surprisingly cosmetic preparations involving W/O emulsions have found little success in the marketplace. This appears to be due to the difficulty in preparing stable W/O emulsions which are cosmetically acceptable (i.e. not waxy, tacky, heavy, draggy) and which will carry sufficient water to have the desired skin moisturizing effect.

A search of the patent art has revealed many patents relating to water-in-oil emulsions generally, but relatively few which have any pertinence with respect to the present invention. There are, however, three prior patents which should be briefly considered at this time.

U.S. Pat. No. 3,594,409 is of interest in disclosing cosmetic W/O emulsions which may contain as much as about 66% water, but this patent is really related to, and all claims are directed to, a special type of emulsifying agent which may be referred to as magnesium salts of succinic esters of polyoxyalkylene fatty alcohols, and which are quite unrelated to the emulsifying agents of the present invention.

U.S. Pat. No. 3,102,128 teaches an ointment base indicated to be capable of forming water-in-oil emulsions by addition of up to three times by weight of water, although no specific examples of such emulsions are provided. The patent is directed to a special type emulsifier referred to as mixed esters of a pentaerythrite di-fatty acid and a citric acid di-fatty alcohol ester in a 1:1 molar ratio; and this special type of emulsifier is quite unrelated to the emulsifying agents of the present invention.

U.S. Pat. No. 3,536,816 disclosed preparation of W/O emulsions employing as emulsifier a partial ester of the monoglyceride of oleic acid but does not indicate that stable emulsions can be prepared containing more than about 43% water. Thus this patent fails to provide any teaching of the high, 60 to 80%, water content of W/O emulsions which are obtained in accordance with the present invention.

THE INVENTION

It has now been discovered in accordance with the present invention that cosmetically attractive, stable water-in-oil (W/O) emulsions containing as much as 60 to 80% water and as much as about 10% covering agent and/or pigment, and which exhibit excellent skin moisturizing properties can be prepared by employing a unique combination of emulsifying agents, and by incorporating in the oil phase components facilitating penetration of the oil phase and entrapped moisture into the skin.

The oil phase which accounts for about 15 to 25% by weight of the new compositions can suitably comprise one or more straight chain hydrocarbon(s) of varying chain length(s) selected to provide the consistency and degree of oiliness and tack desired in the finished product. A significant portion, suitably about 20 to 30%, of the oil phase comprises one or more highly penetrating, biologically compatible saturated or unsaturated branched chain hydrocarbons containing from about 14 to 36 carbon atoms. These act as "carriers" of tiny, moisture-loaded "micro-droplets" of the emulsion of the inner cell layers of the stratum corneum where the water is slowly released and made available to plump the cells.

The stable W/O emulsion is provided by a mixture of emulsifiers comprising about 5 to 10% of the composition and consisting essentially of esters of polymerized polyhydroxyl alcohol with $C_{12}$ to $C_{18}$ fatty acids and lesser amounts of di- or tri-valent metallic soaps, the latter apparently functioning as emulsion stabilizers.

Typical polymers of polyhydroxyl alcohols with $C_{12}$ to $C_{18}$ fatty acid esters to be used as emulsifiers include those having non-ionic characteristics such as:
polyglyceryl-2 sesquioleate
decaglyceryl monooleate
polyglyceryl-4 oleate
triglyceryl di-isostearate
decaglyceryl decaoleate
hexaglyceryl distearate
glyceryl-7-monomyristate
triglyceryl monooleate
hexaglyceryl dioleate
polyglyceryl 4-isostearate
polyglyceryl-6 dioleate As these will differ somewhat in physical properties, selection will be based in part on the particular properties desired in the cosmetic composition.

As emulsion modifiers the metallic soaps can be salts such as magnesium, calcium, barium, aluminum, gallium or zinc salts of fatty acids such as stearic, palmitic, myristic, oleic and octanoic acids, as well as lithium salts of the foregoing acids. It should be noted in this connection that the monovalent sodium and potassium salts and the triethanolamine salts of these acids do not permit the production of stable W/O emulsions, and because of the water-solubility of these soaps the emulsion may even shift to the O/W type. Thus basically the present invention uses the di- and tri-valent salts as well as the lithium salt (as opposed to other monovalent salts which are not effective).

It appears that the combination of the primary emulsifier and the metallic soap is essential to the production of stable W/O emulsions. If the primary emulsifier is omitted the other components of a formulation do not emulsify, and if the metallic soap is eliminated the emulsions which may form are very unstable. As earlier mentioned, selection of the primary emulsifier will depend in part on the physical properties desired in the final product. The same can be said for the selection of the metallic soap to be used in a particular formulation. It will be apparent, however, that both the primary emulsifier and the metallic soap must be present, and that the metallic soap in generally in a somewhat lesser amount, enables those desiring to formulate compositions in accordance with the present invention to readily determine the optimum amounts and proportions of these components for the particular type of product desired.

In formulating different type end products, which may range from simple moisturizing lotions of quite fluid consistency to more complex formulations of the "pancake" make-up type which may have a heavy cream or thixotropic consistency, it will be understood that any of the cosmetic conventional coating and/or coloring agents or pigments can be incorporated if desired in amounts to provide the cosmetic properties desired. While such additives will normally not exceed about 10% of the total weight of the composition, somewhat higher amounts of additives can be used in special-purpose cosmetic formulations without interfering with the stability of the W/O emulsions.

The following examples will serve to show how typical cosmetic water-in-oil emulsions in accordance with the present invention are prepared, but it is to be understood that these examples are given by way of illustration and not of limitation.

EXAMPLE I

A cosmetic make-up composition is prepared containing:

| Component | Parts by Weight |
|---|---|
| Mineral Oil, 50 cp. visc. | 5.55 |
| Petrolatum, 45° C. melting point | 2.25 |
| Polyglyceryl - 6 dioleate | 4.50 |
| Propyl Parasept (propyl parahydroxy benzoate) | 0.10 |
| Perhydro Squalene | 5.85 |
| Robane* | 3.00 |
| Ozoherite Wax | 3.60 |
| Imidazolidinyl Urea (Germall) | 0.15 |
| Methyl Parasept (methyl parahydroxy benzoate) | 0.15 |
| Magnesium Stearate (food grade) | 0.50 |
| Iron Oxide Pigments | 10.00 |
| Deionized Water | 64.35 |

*Robane is a trademark identifying a purified form of a branched hydrocarbon known as squalane and is available from Robeco Chemicals, Inc. of New York, New York.

In formulating this product, the following procedure was used:

Procedure: Heat oil phase (mineral oil, petrolatum, polyglyceryl-6 dioleate, perhydrosqualene, ozokerite wax, Robane, and propyl parasept) to 70° C.

In a separate container, heat water, methyl parahydroxy benzoate and Germall to 72° C. The weight formula quantities of the water phase are heated in a steam jacketed stainless steel kettle provided with a planetary agitator and a homomixer head. Then add the water phase to the oil phase with moderate agitation of the planetary agitator with the homomixer head on. When the mixing is complete (25 r.p.m.), keep on mixing for ten minutes. Then mix only with the planetary agitator at 15 r.p.m. and begin circulating cool water through the jacket. Cool to 60° C. Then add the magnesium stearate and agitate with homomixer on for an additional 10 minutes. At 55° C. add perfume, if any, with homomixer head on for three more minutes. Then cool to 30° and deliver resulting product to storage.

The resulting product has a souffle' creamy consistency permitting easy application to the skin and feathering to provide gradation of color. Repeated application of this product produces a notable firming of the skin to which it is applied due to the skin penetrating and moisturizing effect of the composition.

EXAMPLE II

A composition was prepared as at Example I, but eliminating the 4.5 parts by weight of polyglyceryl-6 dioleate. As thus modified, the blended components failed to form an emulsion.

EXAMPLE III

The composition was prepared as described in Example I, but substituting for the magnesium stearate an equivalent amount of triethanolmine stearate. As a result of this change, the emulsion formed was an unstable emulsion of the O/W type which stratified into separate layers upon centrifuging at 2500 r.p.m. for 30 minutes.

The same basic procedure described in Example I was used in preparing Examples IV to VIII, except the temperatures used in preparing the oil and water phase was as follows:

| Example | Oil Phase | Water Phase |
|---|---|---|
| IV | 70° C. | 72° C. |
| V | 78° C. | 80° C. |
| VI | 78° C. | 80° C. |
| VII | 70° C. | 72° C. |
| VIII | 78° C. | 80° C. |

The metal salt was added after emulsification in all cases. All percentages shown are weight percent unless otherwise indicated.

The resulting emulsions were stable water-in-oil (W/O) emulsions exhibiting excellent skin moisturizing properties and illustrate the use of aluminum, barium, zinc and lithium salts.

EXAMPLE IV

| | % |
|---|---|
| Polyglyceryl-6 dioleate | 5.000 |
| Snow White petrolatum | 2.500 |
| Tegosept P | 0.100 |
| Carnation oil | 8.000 |
| Ozokerite | 4.000 |
| Robane | 4.000 |
| Squalene | 4.000 |
| Alpha tocopherol acetate | 0.100 |
| Vitamin A & D 1000/200 | 0.200 |
| Germall | 0.150 |
| Tegosept M | 0.150 |
| Deionized Water | 71.300 |
| Aluminum stearate | 0.500 |

EXAMPLE V

| | % |
|---|---|
| Polyglyceryl-2-sesquioleate | 5.000 |
| Snow White petrolatum | 2.50 |
| Tegosept P | 0.10 |
| Amerchol L-101 | 8.00 |
| Ozokerite | 2.00 |
| Super Hartolan | 2.00 |
| Squalene | 4.00 |
| Alpha Tocopherol Acetate | 0.10 |
| Vitamin A & D 1000/200 | 0.20 |
| Robane | 4.00 |
| Deionized Water | 68.30 |
| Tegosept M | 0.15 |
| Germall | 0.15 |
| Glycerine | 3.00 |
| Barium Stearate | 0.50 |

EXAMPLE VI

| Triglyceryl Monostearate | 5.00 |
|---|---|
| Snow White Petrolatum | 2.50 |
| Tegosept P | 0.10 |
| Amerchol L-101 | 8.00 |
| Ozokerite | 2.00 |
| Super Hartolan | 2.00 |
| Squalene | 4.00 |
| Alpha Tocopherol Acetate | 0.10 |
| Vitamin A & D 1000/200 | 0.20 |
| Robane | 4.00 |
| Deionized Water | 68.30 |
| Tegosept M | 0.15 |
| Germall | 0.15 |
| Glycerine | 3.00 |
| Aluminum Stearate | 0.50 |

EXAMPLE VII

| | % |
|---|---|
| Polyglyceryl-4-Oleate | 4.500 |
| Snow White Petrolatum | 2.250 |
| Tegosept P | 0.100 |
| Carnation Oil | 8.550 |
| Ozokerite | 3.600 |
| Robane | 5.850 |
| Deionized Water | 64.350 |
| Germall | 0.150 |
| Tegosept M | 0.150 |
| BS-080 (Pigment Blends made | 5.000 |
| BS-076 up of iron oxides) | 5.000 |
| Zinc Stearate | 0.500 |

EXAMPLE VIII

| Hostacerin* | 5.00 |
|---|---|
| Snow White Petrolatum | 2.50 |
| Tegosept P | 0.10 |
| Carnation Oil | 8.00 |
| Ozokerite | 4.00 |
| Robane | 4.00 |
| Squalene | 4.00 |
| Alpha Tocopherol Acetate | 0.10 |
| Vitamin A & D 1000/200 | 0.20 |
| Deionized Water | 68.30 |
| Tegosept M | 0.15 |
| Germall | 0.15 |
| Glycerine | 3.00 |
| Lithium Stearate | 0.50 |

*American Hoeschst product: polyglyceryl-2-sesquioleate—;

The beneficial skin moisturizing properties of the cosmetic preparations in accordance with the present invention are considered to be the result of a combination of the water-in-oil (W/O) form of the emulsion and the inclusion of the branched-chain hydrocarbon penetrating oils in the oil phase. As the dispersed microdroplets of water are carried to the inner skin layers by the penetrating oils, the oils are diluted by the skin's own oils breaking the emulsion and releasing the water. Emulsion breakage is believed to be further accelerated by the skin's electrolytes. The amount of water released varies from about 2.5 to 10 parts of water per part of oil absorbed depending upon whether the total oil phase is absorbed or only the penetrating oils, or mixtures of both.

Various changes and modifications in the cosmetic water-in-oil emulsions as herein described may occur to those skilled in the art, and to the extent that such changes and modifications are embraced by the appended claims, it is to be understood that they constitute part of the present invention.

What is claimed is:

1. A cosmetic make-up composition consisting of

| | Parts by Weight |
|---|---|
| Mineral Oil 50 cp. visc. | 5.55 |
| Petrolatum, 45° C. melting point | 2.25 |
| Polyglyceryl-6-dioleate | 4.50 |
| Propyl para-hydroxy benzoate | 0.10 |
| Perhydro Squalene | 5.85 |
| Squalane | 3.00 |
| Ozokerite Wax | 3.60 |
| Imidazolidinyl Urea (Germall) | 0.15 |
| Methyl para-hydroxy benzoate | 0.15 |
| Magnesium Stearate (Food grade) | 0.50 |
| Iron Oxide Pigments | 10.00 |
| Deionized Water | 64.35 |

2. A stable moisturizing cosmetic composition of

| | % |
|---|---|
| Polyglyceryl-6 dioleate | 5.00 |
| Snow White petrolatum | 2.50 |
| Propyl p-hydroxy benzoate | 1.00 |
| Ozokerite wax | 4.00 |
| Squalane | 4.00 |
| Squalene | 4.00 |
| Alpha tocopherol acetate | 0.10 |
| Vitamin A and D 1000/200 | 0.20 |
| Propyl p-hydroxy benzoate | 0.10 |
| Methyl p-hydroxy benzoate | 0.15 |
| Imidazolidinyl urea | 0.15 |
| Aluminum stearate | 0.50 |
| Deionized water | 71.30 |

3. A stable moisturizing cosmetic composition consisting of

| | % |
|---|---|
| Polyglyceryl-2-sesquioleate | 5.00 |
| Snow White Petrolatum | 2.50 |
| Propyl p-hydroxy benzoate | 0.10 |
| Amerchol L-101 | 8.00 |
| Ozakerite | 2.00 |
| Super Hartolan | 2.00 |
| Squaline | 4.00 |
| Alpha Tocopherol Acetate | 0.10 |
| Vitamin A and D 1000/200 | 0.20 |
| Robane | 4.00 |
| Methyl p-hydroxy benzoate | 0.15 |
| Imidazolidinyl Urea | 0.15 |

-continued

|  | % |
|---|---|
| Glycerine | 3.00 |
| Barium Stearate | .50 |
| Deionized water | 68.30 |

4. A stable moisturizing cosmetic composition consisting of

|  | % |
|---|---|
| Triglyceryl monostearate | 5.00 |
| Snow White petrolatum | 2.50 |
| Ozokerite | 2.00 |
| Amerchol L-101 | 8.00 |
| Super Hartolan | 2.00 |
| Squalene | 4.00 |
| Squalane | 4.00 |
| Alpha tocopherol acetate | 0.10 |
| Vitamin A and D 1000/200 | 0.20 |
| Propyl p-hydroxy benzoate | 0.10 |
| Methyl p-hydroxy benzoate | 0.15 |
| Imidazolidinyl urea | 0.15 |
| Aluminum Stearate | 0.50 |
| Gylcerine | 3.00 |
| Water | 68.30 |

5. A stable moisturizing cosmetic composition consisting of

|  | % |
|---|---|
| Polyglycerol-4-oleate | 4.50 |
| Snow White Petrolatum | 2.25 |
| Carnation Oil | 8.55 |
| Ozokerite | 3.60 |
| Squalane | 5.85 |
| Propyl p-hydroxy benzoate | 0.10 |
| Methyl p-hydroxy benzoate | 0.15 |
| Imidazolidinyl urea | 0.15 |
| Pigment blends made up of Iron oxides | 10.00 |
| Zinc stearate | 0.50 |
| Deionized water | 64.35 |

6. A stable moisturizing cosmetic composition consisting of

|  | % |
|---|---|
| Polyglyceryl-2-sesquioleate | 5.00 |
| Snow White Petrolatum | 2.50 |
| Carnation Oil | 8.00 |
| Ozokerite | 4.00 |
| Squalene | 4.00 |
| Squalane | 4.00 |
| Alpha tocopherol acetate | 0.10 |
| Vitamin A and D 1000/200 | 0.20 |
| Propyl p-hydroxy benzoate | 0.10 |
| Methyl p-hydroxy benzoate | 0.15 |
| Imidazolidinyl urea | 0.15 |
| Lithium stearate | 0.50 |
| Glycerine | 3.00 |
| Deionized Water | 68.30 |

* * * * *